US 9,846,142 B2

(12) United States Patent
Royyuru (10) Patent No.: US 9,846,142 B2
(45) Date of Patent: *Dec. 19, 2017

(54) PRESENTING STRETCHED STRANDS OF SINGLE STRAND DNA FOR SEQUENCING DOUBLE STRAND DNA

(71) Applicant: International Business Machines Corporation, Armonk, NY (US)

(72) Inventor: Ajay K. Royyuru, Congers, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 238 days.

This patent is subject to a terminal disclaimer.

(21) Appl. No.: 14/746,182

(22) Filed: Jun. 22, 2015

(65) Prior Publication Data

US 2015/0315638 A1    Nov. 5, 2015

Related U.S. Application Data

(63) Continuation of application No. 14/608,741, filed on Jan. 29, 2015.

(Continued)

(51) Int. Cl.
*G01N 27/327* (2006.01)
*G01N 27/447* (2006.01)
*C12Q 1/68* (2006.01)
*B01L 3/00* (2006.01)
*G01N 33/487* (2006.01)

(52) U.S. Cl.
CPC .. *G01N 27/44704* (2013.01); *B01L 3/502761* (2013.01); *C12Q 1/6869* (2013.01);
(Continued)

(58) Field of Classification Search
CPC .................................................. G01N 33/48721
See application file for complete search history.

(56) References Cited

U.S. PATENT DOCUMENTS

2015/0315637 A1   11/2015   Royyuru
2015/0316504 A1   11/2015   Royyuru

OTHER PUBLICATIONS

Venta et al, Differentiation of Short, Single-Stranded DNA Homopolymers in Solid-State Nanopores, ACSNANO, vol. 7, No. 5, 4629-4636, 2013.*

(Continued)

*Primary Examiner* — Alexander Noguerola
(74) *Attorney, Agent, or Firm* — Cantor Colburn LLP; Vazken Alexanian (57) ABSTRACT

A mechanism is provided for presenting single strands of a double strand molecule to a membrane. The double strand molecule is driven to a first side of the membrane by an electric field. The membrane has a first and second nanopore spaced apart by a nanopore separation distance. The first strand of the double strand molecule is captured in the first nanopore when driven to the first side of the membrane. The second strand is captured in the second nanopore by having the nanopore separation distance between the first nanopore and the second nanopore corresponding to a strand separation distance between the first and second strands, and/or by having captured the first strand to limit diffusion of the second strand. The first and second strands respectively in the first and second nanopores are individually stretched, by the first and second strands recombining on the second side of the membrane.

14 Claims, 5 Drawing Sheets

Related U.S. Application Data (60) Provisional application No. 61/986,364, filed on Apr. 30, 2014.

(52) U.S. Cl.
CPC ..... *G01N 27/447* (2013.01); *G01N 27/44791* (2013.01); *G01N 33/48721* (2013.01); *B01L 2200/0663* (2013.01); *B01L 2400/0421* (2013.01)

(56) References Cited

OTHER PUBLICATIONS

Supporting Informaiton for Venta et al, Differentiation of Short, Single-Stranded DNA Homopolymers in Solid-State Nanopores, ACSNANO, vol. 7, No. 5, 4629-4636, 2013.*

Raza et al., "Crosstalk between adjacent nanopores in a solid-state membrane array for multi-analyte high-throughput biomolecule detection," Journal for of Applied Physics 120, 064701 (2016).*
Gadaleta et al., "Sub-additive ionic transport across arrays of solid-state nanoopres," Physics of Fluids 26, 012005 (2014).*
Schmidt et al., "Nanopore arrays in a silicon membrane for parallel single-molecule detection: fabrication," Nanotechnology 26.*
Article on Deoxyribonucleic acid (DNA) by Robert Stewart from the online Virtual Cell Radiobiology Software Manual, downloaded Apr. 11, 2017.*
List of IBM Patents or Patent Applications Treated as Related; Date Filed: Jun. 22, 2015, pp. 1-2.
Jun et al., "Rapid Fabrication of Uniformly Sized Nanopores and Nanopore Arrays for Parallel DNA Analysis", Advanced Materials, DOI: 10.1002/adma.200601191, 2006, pp. 1-5.
Meller Group, "Fabrication of Solid-state nonopores and nanopore arrays", Single Molecule Biophysics & Nano-biotechnology, BME, 2006, p. 1.

* cited by examiner

```
┌─────────────────────────────────────────────────────────────┐
│ Drive the double strand molecule to a first side of the    │
│ membrane by an electric field, the membrane comprising a   │
│ first nanopore and a second nanopore spaced apart by a     │
│ nanopore separation distance, the membrane comprising a    │
│ second side opposite the first side 405                    │
└─────────────────────────────────────────────────────────────┘
                              │
                              ▼
┌─────────────────────────────────────────────────────────────┐
│ The double strand molecule comprises a first strand and a │
│ second strand when driven to the first side of the         │
│ membrane 410                                                │
└─────────────────────────────────────────────────────────────┘
                              │
                              ▼
┌─────────────────────────────────────────────────────────────┐
│ Cause the first strand of the double strand molecule to be │
│ captured in the first nanopore by the electric field when  │
│ the double strand molecule is driven to the first side of  │
│ the membrane 415                                            │
└─────────────────────────────────────────────────────────────┘
                              │
                              ▼
┌─────────────────────────────────────────────────────────────┐
│ Cause the second strand of the double strand molecule to   │
│ be captured in the second nanopore by having the nanopore  │
│ separation distance between the first nanopore and the     │
│ second nanopore corresponding to a strand separation       │
│ distance between the first strand and the second strand,   │
│ by having captured the first strand to limit diffusion of  │
│ the second strand, and/or by both 420                      │
└─────────────────────────────────────────────────────────────┘
                              │
                              ▼
┌─────────────────────────────────────────────────────────────┐
│ Individually stretch the first strand in the first         │
│ nanopore and the second strand in the second nanopore      │
│ which is caused by the first strand and the second strand  │
│ recombining on the second side of the membrane 425         │
└─────────────────────────────────────────────────────────────┘
```

FIG. 5

PRESENTING STRETCHED STRANDS OF SINGLE STRAND DNA FOR SEQUENCING DOUBLE STRAND DNA

DOMESTIC PRIORITY

This application claims priority to U.S. application Ser. No. 14/608,741, filed Jan. 29, 2015, which claims priority to U.S. Provisional Application Ser. No. 61/986,364, filed Apr. 30, 2014, which are incorporated herein by reference in their entirety.

BACKGROUND

The present invention relates to nanopore devices, and more specifically, to presenting single strands of DNA or RNA molecules to a membrane from double strands of DNA or RNA.

Nanopore sequencing is a method for determining the order in which nucleotides occur on a strand of deoxyribonucleic acid (DNA). A nanopore (also referred to a pore, nanochannel, hole, etc.) can be a small hole in the order of several nanometers in internal diameter. The theory behind nanopore sequencing is about what occurs when the nanopore is submerged in a conducting fluid and an electric potential (voltage) is applied across the nanopore. Under these conditions, a slight electric current due to conduction of ions through the nanopore can be measured, and the amount of current is very sensitive to the size and shape of the nanopore. If single bases or strands of DNA pass (or part of the DNA molecule passes) through the nanopore, this can create a change in the magnitude of the current through the nanopore. Other electrical or optical sensors can also be positioned around the nanopore so that DNA bases can be differentiated while the DNA passes through the nanopore.

The DNA can be driven through the nanopore by using various methods, so that the DNA might eventually pass through the nanopore. The scale of the nanopore can have the effect that the DNA may be forced through the hole as a long string, one base at a time, like thread through the eye of a needle. Recently, there has been growing interest in applying nanopores as sensors for rapid analysis of biomolecules such as deoxyribonucleic acid (DNA), ribonucleic acid (RNA), protein, etc. Special emphasis has been given to applications of nanopores for DNA sequencing, as this technology holds the promise to reduce the cost of sequencing below $1000/human genome.

SUMMARY

According to an embodiment, a method is provided for presenting single strands of a double strand molecule to a membrane. A double strand molecule is driven to a first side of the membrane by an electric field, where the membrane includes a first nanopore and a second nanopore spaced apart by a nanopore separation distance. The membrane includes a second side opposite the first side. The double strand molecule comprises a first strand and a second strand when driven to the first side of the membrane. The first strand of the double strand molecule is caused to be captured in the first nanopore by the electric field when the double strand molecule is driven to the first side of the membrane. The second strand of the double strand molecule is caused to be captured in the second nanopore by having the nanopore separation distance between the first nanopore and the second nanopore corresponding to a strand separation distance between the first strand and the second strand, by having captured the first strand to limit diffusion of the second strand, and/or both by having the nanopore separation distance between the first nanopore and the second nanopore corresponding to a strand separation distance between the first strand and the second strand and by having captured the first strand to limit diffusion of the second strand. The first strand in the first nanopore and the second strand in the second nanopore are individually stretched, which is caused by the first strand and the second strand recombining on the second side of the membrane.

According to an embodiment, a system is provided for presenting single strands of a double strand molecule to a membrane. The system includes a membrane comprising a first side opposite a second side opposite, where the double strand molecule driven to the first side of the membrane by an electric field from a voltage source. The membrane includes a first nanopore and a second nanopore spaced apart by a nanopore separation distance. A first reservoir is on the first side. The double strand molecule is introduced on the first side and comprises a first strand and a second strand when driven to the first side of the membrane. The voltage source causes the first strand of the double strand molecule to be captured in the first nanopore by the electric field when the double strand molecule is driven to the first side of the membrane. The second strand of the double strand molecule is captured in the second nanopore by having the nanopore separation distance between the first nanopore and the second nanopore corresponding to a strand separation distance between the first strand and the second strand, by having captured the first strand to limit diffusion of the second strand, and/or both by having the nanopore separation distance between the first nanopore and the second nanopore corresponding to a strand separation distance between the first strand and the second strand and by having captured the first strand to limit diffusion of the second strand. A second reservoir is on the second side, where the first strand in the first nanopore and the second strand in the second nanopore are individually stretched by the first strand and the second strand recombining on the second side of the membrane in the second reservoir.

Additional features and advantages are realized through the techniques of the present invention. Other embodiments and aspects of the invention are described in detail herein and are considered a part of the claimed invention. For a better understanding of the invention with the advantages and the features, refer to the description and to the drawings.

BRIEF DESCRIPTION OF THE SEVERAL VIEWS OF THE DRAWINGS

The subject matter which is regarded as the invention is particularly pointed out and distinctly claimed in the claims at the conclusion of the specification. The forgoing and other features, and advantages of the invention are apparent from the following detailed description taken in conjunction with the accompanying drawings in which:

DETAILED DESCRIPTION

Sequencing of DNA with nanopore technologies requires the presentation of single strand DNA to the base sensing module. One particular challenge is to present the single strand in stretched configuration to the base sensing module. This stretching is required to provide maximum spatial separation of DNA bases of the single strand. Failure to achieve stretching allows multiple bases to simultaneously interact with the base sensing module, thereby reducing the fidelity and resolution of sequencing.

An embodiment provides a technique and mechanism for presenting stretched strands of single strand DNA for the purpose of sequencing double strand (stranded) DNA.

Figure 1:
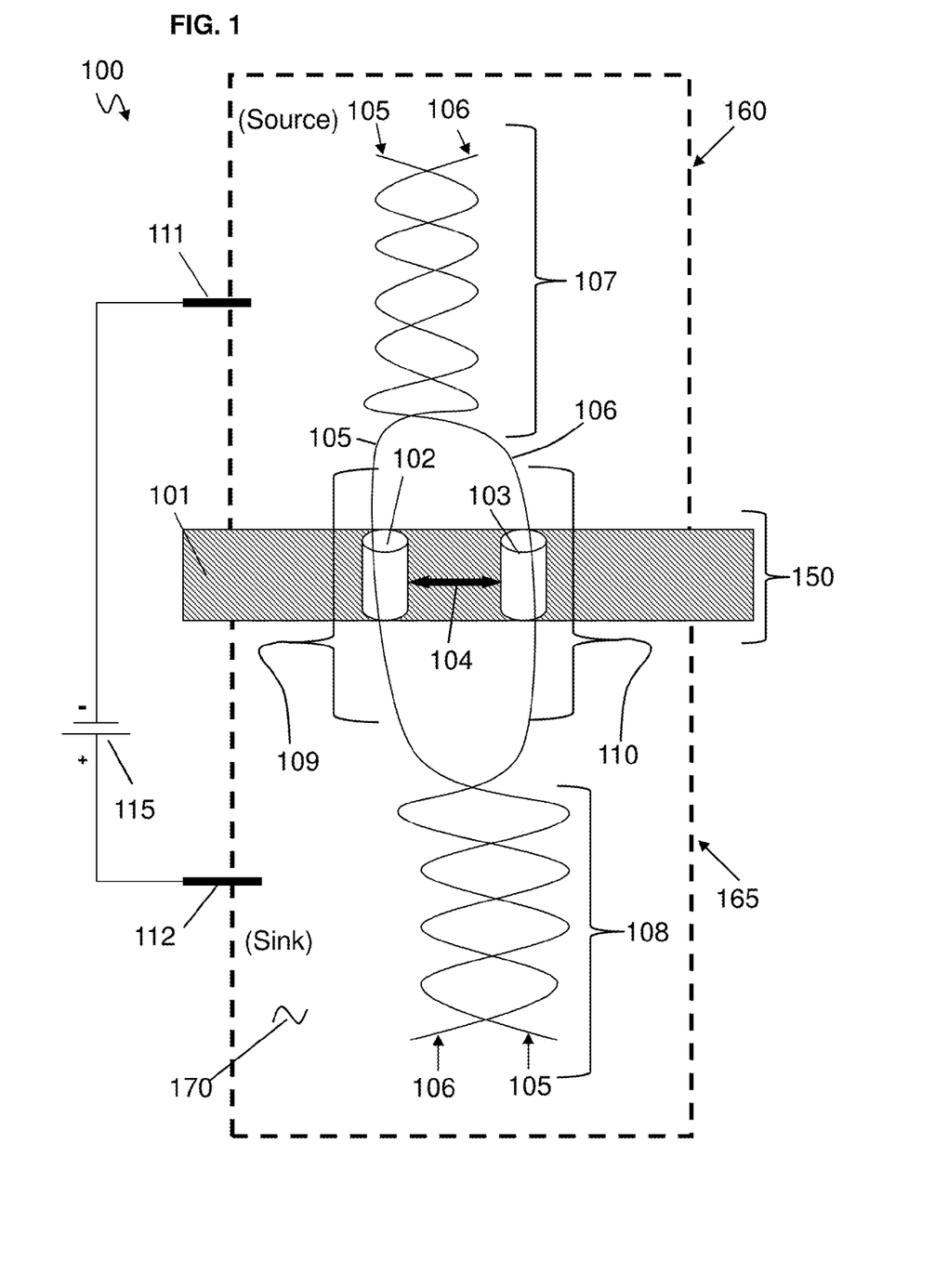
FIG. 1 is a schematic of a dual nanopore/nanochannel presentation and detection system according to an embodiment.

Now turning to the figures, FIG. 1 is a schematic of a system 100 according to an embodiment. The system 100 includes a nanodevice 150. The nanodevice 150 includes a membrane 101. The membrane 101 includes a nanopore 102 and a nanopore 103. In one case, the nanopores 102 and 103 may each be nanochannels, and it is contemplated that nanochannels and any nano-opening can be utilized as discussed herein according to embodiments as would be understood to one skilled in the art. Each nanopore 102 and 103 may be 1 to 2 nanometers (nm) in nanopore diameter or nanochannel size (e.g., width).

The membrane 101 may be silicon, silicon dioxide, or any insulating material. Also, the nanopores 102 and 103 may be the combination of two attached proteins.

A nanopore separation distance 104 is shown as the distance separating the nanopore 102 from the nanopore 103 in the membrane 101. A top reservoir 160 (cis or source side) is sealed to the top side of the membrane 101 and a bottom reservoir 165 (trans or sink side) is sealed to the bottom side of the membrane 101. Electrode 111 is in the top reservoir 160 and electrode 112 is in the bottom reservoir 165. Electrode 111 is connected to a negative side of a voltage source 115 and electrode 112 is connected to the positive side of the voltage source 115. An electrically conductive solution 170 fills the top reservoir 160, bottom reservoir 165, nanopore 102, and nanopore 103.

As an example, a double strand DNA molecule 107 may be introduced into the top reservoir 160 by typical means such as a syringe, pump, etc. The double strand DNA molecule 107 may be referred to as the target molecule for testing.

Double stranded DNA is normal and abundant, e.g., genomic DNA is almost entirely double stranded. An embodiment of the present invention allows direct handling and sequencing of double stranded DNA molecules, and eliminates the sample preparation steps (e.g., fragmentation and melting) required for single strand sequencing devices. The embodiment allows for sequencing of virtually unlimited lengths of DNA, since double strand DNA is stable for virtually unlimited lengths, which is an advantage over single strand sequencing devices where the read lengths are limited by stability of single strand DNA molecules.

Operation of the nanodevice 150 in the system 100 translocates double strand DNA from the top reservoir 160 (source) to the bottom reservoir 165 (sink). Unwinding (i.e., base pair opening on source side) and helical rewinding (i.e., base pairing on sink side) is discreet (i.e., base pair by base pair); therefore, the nanodevice 150 achieves ratcheting of double stranded DNA through the device.

The double strand DNA molecule 107 has a single strand DNA molecule 105 and a single strand DNA 106. The single strand DNA molecule 105 has a sequence that is complementary to the sequence of single strand DNA 106. This causes the two strands to hybridize into double stranded DNA 108 in certain normal conditions (e.g., temperature below melting temperature).

Hybridization of single strands into double strand configuration on both sides (source side and sink side) of the membrane 101 naturally extends along the length of the available molecules, to a physical proximity of pore openings of nanopores 102 and 103. As the double strand DNA molecule 107 in the top reservoir 160 is driven to the membrane 101, the single strand DNA 105 is captured in nanopore 102 (for example) and the other single strand DNA 106 is capture in the other close by nanopore 103. As the energetics of hybridization favor double strand configuration over single strand configuration, the hybridization extends to as close a proximity of nanopores 102 and 103 because of the small nanopore separation distance 104 and the flexibility of stretched single strand region 109 of single strand DNA 105 and stretched single strand region 110 of single strand DNA 106. The energetics naturally drive for a minimization of stretched single stranded regions 109 and 110, thereby stretching the single strand DNA 105 at the stretched single strand region 109 and stretching the single strand DNA 106 at the stretched single strand region 110 respectively through the nanopores 102 and 103.

Further details regarding operation of the system 100 are now discussed. The double strand DNA molecule 107 is introduced in the top reservoir 160. The double strand DNA molecule 107 is negatively charged. The double strand DNA molecule 107 is presented on the source side of the membrane 101. For example, the voltage source 115 applies a positive voltage to electrode 112 and negative voltage to electrode 111, which generates an ionic current through the electrically conductive solution 170, and an upward pointing electric field (resulting in a downward force on the double strand DNA molecule 107). The negative voltage and downward force translocate the negatively charged double strand DNA molecule 107 from the source side of the membrane to the sink side through the openings which may be nanopores/ nanochannels 102 and 103 in the membrane 101. The electrical field induced by the voltage source 115 (i.e., the circuit of the electrodes 111 and 112, the voltage source 115, and electrically conductive solution 170) causes capture of one strand such as the single strand DNA 105 in one nanopore/channel such as the nanopore 102.

The capture of the single strand DNA 105 in nanopore 102 limits the diffusion of the other single strand DNA 106 to the proximity of the nanopore 102, as the molecular region of the source side is hybridized as the double strand DNA molecule 107. This limitation of diffusion of the single strand DNA 106 provides an enhanced capture rate for the single strand DNA 106 to be captured by the electric field through nanopore 103 (because the single strand DNA 106 is confined to the close proximity of nanopore 102 which is only separated from nanopore 103 by nanopore separation distance 104 which can be a few nanometers). The single strand DNA 105 is bound to the single strand DNA 106 at the point of hybridization (on the double strand DNA molecule 107), and this prevents the single strand DNA 106 from leaving the area of the nanopore 103.

Accordingly, the single strand DNA 106 is captured in the nanopore 103 while the single strand DNA 105 is in the nanopore 102 (e.g., the single strand DNA 105 is being threaded through the nanopore 103 as the voltage of the voltage source 115 is applied). Now, as the electrical field from the voltage of the voltage source 115 connected to electrodes 111 and 112 translocates the two single strands 105 and 106 through respective nanopores 102 and 103, these strands (single strand 105 and single strand 106) move into the sink side of membrane 101 in bottom reservoir 165.

As the length of the two molecules (i.e., single strand DNA 105 and single strand DNA 106) on the sink side exceeds the minimum required (e.g., usually 10-12 bases on each strand) the two strands (single strand DNA 105 and single strand DNA 106) hybridize on the sink side in the bottom reservoir 165. The hybridized single strand DNA 105 and single strand DNA 106 is labeled as 108, which is now a double strand DNA molecule 108 on the sink side in the bottom reservoir 165.

Accordingly, the single strand DNA molecules 105 and 106 are the double strand DNA molecule 107 on the source side. The single strand DNA molecules 105 and 106 individually translocate through nanopores 102 and 103 respectively, and then hybridize (rewind) to form the double strand DNA molecule 108. As noted above, the energetics of hybridization favor double strand configuration over single strand configuration. The hybridization (rewinding) on the sink side continuously forming the double strand DNA molecule 108 (until the double strand DNA molecule 107 on the source side has been fed through the nanopores 102 and 103) causes the stretched single strand region 109 of single strand DNA 105 and the stretched single strand region 110 of single strand DNA 106. This stretching (of the single strand DNA molecules 105 and 106) occurs because of the hybridization (rewinding) pulls against the force of the unwinding by the double strand DNA molecule 107. Pulling in opposite directions occurs while the single strand DNA molecule 105 is being stretched in nanopore 102 and the single strand DNA molecule 106 is being stretched in nanopore 103. Since the energetics naturally drive for a minimization of single stranded region 109 and 110, the single stands 105 and 106 are straightened out in these regions for base sequencing (as discussed in an example in FIG. 2.

The following options to improve initial capture of the single strand DNA molecule 105 in the nanopore 102 (in this example). The double strand DNA molecule 107 terminates with a single strand overhang (i.e., a few nanometers). For example, the single strand DNA 105 is longer than single strand DNA 106 of the double strand DNA molecule 107. This availability of unpaired single strand DNA enhances the initial capture of single strand 105 into nanopore 102 or 103.

As another option to increase capture of the single strand DNA molecule 105 and/or the single strand DNA molecule 106, the double strand DNA molecule 107 terminates with non-complementary ends (i.e., with non-complementary bases). This is achieved by enzymatic ligation of short oligomeric non-complementary DNA fragments to single strand 105 and single strand 106. For example, (A)_10 attached to the terminals of both strands will create a frayed non-hybridized terminal that will always remain single strand and increase the efficiency of capture of each single strand DNA molecule (ssDNA) 105 and 106 into the respective nanopores 102 and/or 103 (respectively). In other words, the terminating ends of the single strand 105 and single strand 106 may end with the same (non-complementary) base.

Figure 3:
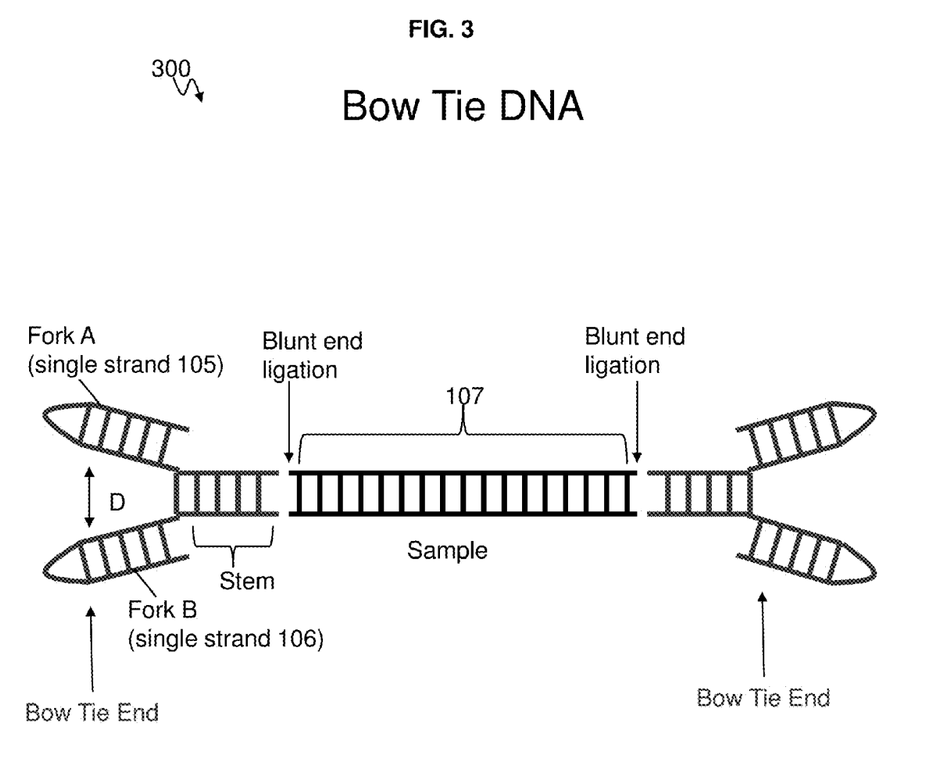
FIG. 3 illustrates a bow tie DNA molecule ligated to the double strand molecule in which formation of a first fork and second fork of a bow tie end promote individual capture in the nanopores according to an embodiment.

As another option, FIG. 3 shows a bow tie DNA molecule 300 according to an embodiment. The double strand DNA molecule 107 terminates with Y shaped double stranded ends (i.e., forked ends). This is achieved by ligation of custom synthesized Y shaped DNA fragments to single strands 105 and 106. This increases the physical separation distance "D" between terminal ends (i.e., between single strands 105 and 106), and allows the nanodevice 150 to function with larger a nanopore separation distance 104.

Another advantage is that nanopore 102 and 103 can also be larger, and these need to be size selective to double stranded DNA. For example, the nanopores 102 and 103 can have an approximately (~) 10 nm diameter when the bow tie DNA molecule 300 is utilized. When the bow tie DNA molecule 300 is not ligated to the double strand molecule 107, the nanopores 102 and 103 may be less than 2 nm (e.g., 1 nm).

The bow tie DNA 300 has a bow tie end on each end. The bow tie end has two forks, shown as fork A and fork B (which respectively correspond to single strands 105 and 106 in FIGS. 1 and 2). Operation of the system 200 applies for the forks A and B as discussed herein for single strand DNA 105 and 106 respectively.

The forks A (single strand DNA 105) and B (single strand DNA 106) have a separation distance D that is matched (e.g., equal to or nearly equal to the nanopore separation distance 104). The forks A and B are connected to a stem (double strand DNA). The stem of the bow tie end is ligated to the double strand DNA molecule 107 for sampling. Note that the options to increase capture rate discussed above also apply for the bow tie DNA 300. For example, forks A and B may terminate with non-complementary ends (i.e., with non-complementary bases) and/or fork A may have an overhang as compared to fork B, both of which enhance the capture of the single strands 105 and 106.

Further information regarding the bow tie DNA is found in filed patent application "Bow Tie DNA Compositions And Methods" IBM®, Application No. 61/986,343 (concurrently filed with Application No. 61/986,364), which is herein incorporated by reference in its entirety.

Figure 2:
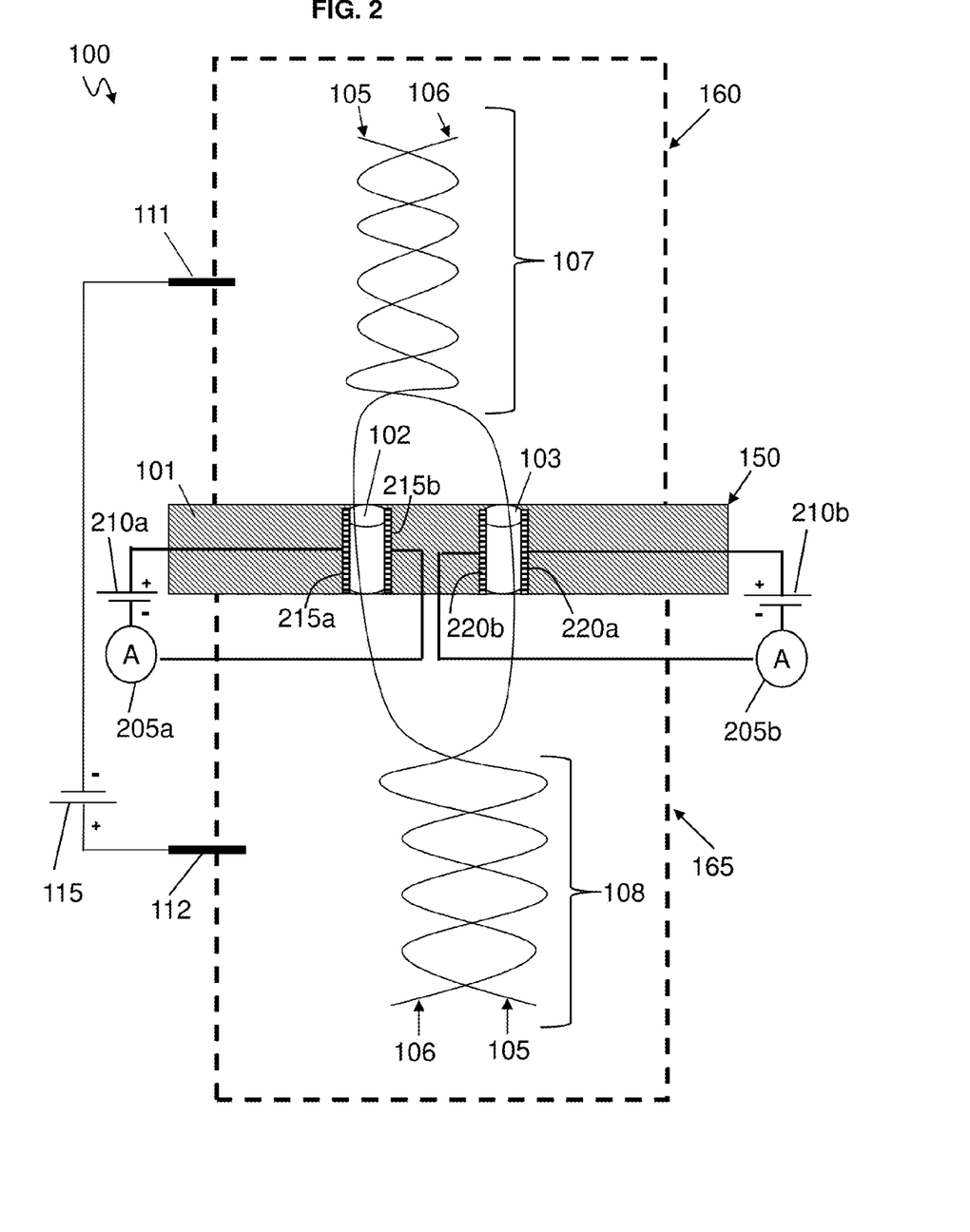
FIG. 2 is a schematic of the system which shows an example of additional elements that may be utilized to individually sequence one single strand and individually sequence another single strand translocating through respective nanopores according to an embodiment.

According to an embodiment, FIG. 2 is a schematic of the system 100 which shows an example of additional elements that may be used to individually sequence the single strand DNA 105 and sequence the single strand DNA 106 translocating through the nanopores 102 and 103. Some elements in FIG. 1 are omitted from the system 200 in FIG. 2 so as not to obstruct the view, but it is understood that the omitted elements are present in the system 200 as discussed herein.

In FIG. 2, a pair of electrodes 215a and 215b are in the nanopore 102 and a pair of electrodes 220a and 220b are in the nanopore 103. The pair of electrodes 215a and 215b are connected to a voltage source 210a and ammeter 205a. The pair of electrodes 220a and 220b are connected to a voltage source 210b and ammeter 205b.

As the stretched single strand DNA 105 passes through the nanopore 102, a base of the single strand 105 is sequenced by applying voltage of the voltage source 210a and by measuring the tunneling current (via ammeter 205a) interacting with the base (in the nanopore 102). Each individual base of the single strand DNA 105 (in the stretched region 109) passing through the nanopore 102 can be identified by its respective tunneling current (i.e., change in tunneling current according to the particular base in the nanopore) as understood by one skilled in the art. Likewise, the complementary base on the single strand DNA 106 in the nanopore 103 is identified (sequenced) by applying voltage of the voltage source 210b and then measuring (via ammeter 205b) the tunneling current. Accordingly, each individual base of the single strand DNA 106 (in the stretched single strand region 110) passing through the nanopore 103 can be identified by its respective tunneling current.

By having the single strand DNA 105 and single strand DNA 106 stretched in respective stretched single strand regions 109 and 110 allows a single base to be in respective nanopores 102 and 103 (each one) at a time, when the sample is the double strand molecule 107. This allows the double strand molecule 107 to be presented as single strands for sequencing without having to change the double strand molecule 107 into two separate (non-connected) strands.

Figure 4:
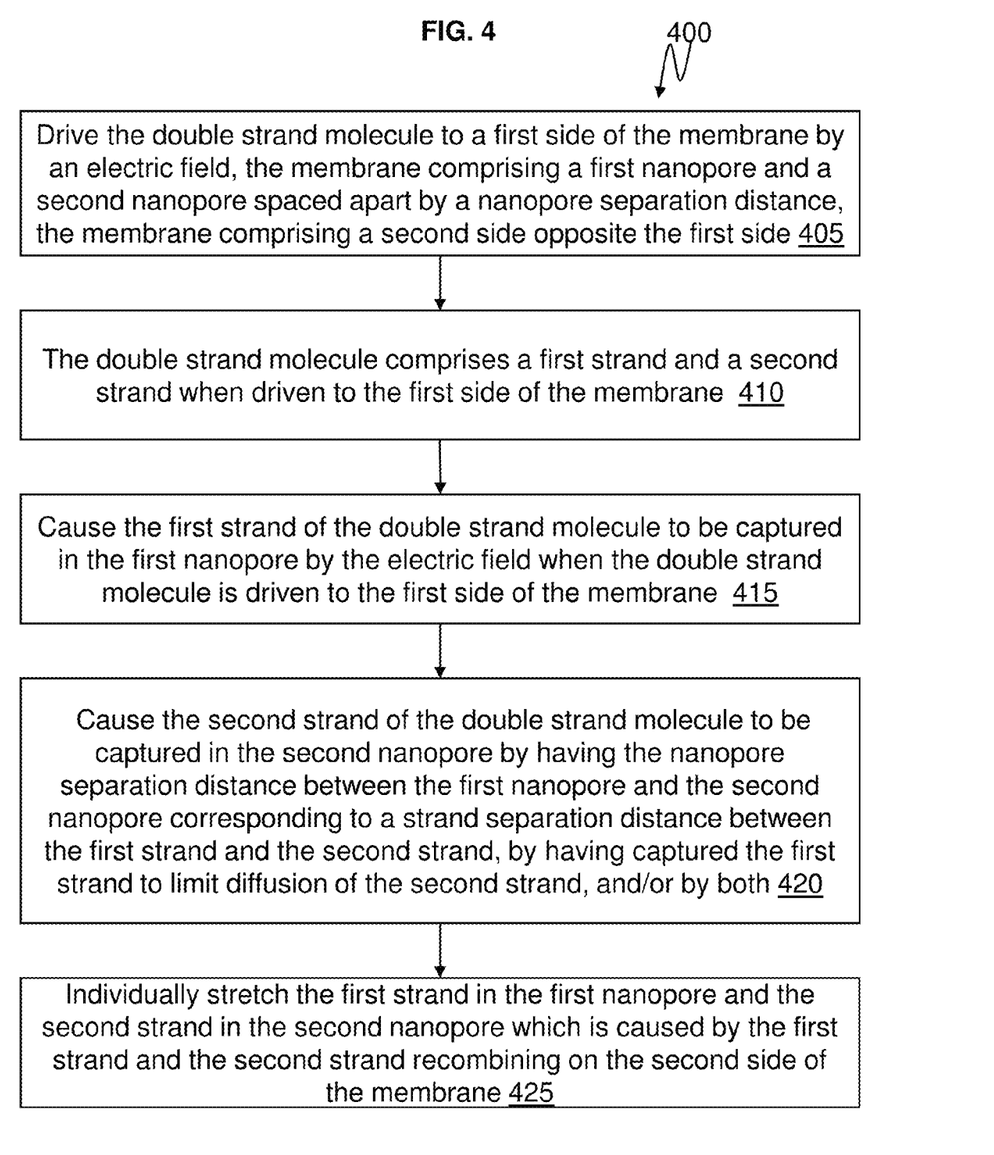
FIG. 4 is a flowchart of a method for respectively presenting two single strands of a double strand molecule to a membrane for individual sequencing according to an embodiment.

FIG. 4 is a flowchart of a method 400 for presenting single strands of a double strand molecule 107 (e.g., target molecule) to a membrane 101 according to an embodiment. Reference can be made to FIGS. 1-3 discussed herein (along with FIG. 5 below).

Voltage of the voltage source 115 drives the (negatively charged) double strand molecule 107 to the first side of the membrane 101 by an electric field at block 405. The membrane 101 includes a first nanopore 102 and a second nanopore 103 spaced apart by the nanopore separation distance 104. The second side (sink side) of the membrane 101 is opposite the first side (source side).

The double strand molecule 107 includes a first single strand 105 and a second single strand 106 when driven to the first side of the membrane 101 in the top reservoir 160 at block 410.

Voltage of the voltage source 115 causes the first single strand 105 of the double strand molecule 107 to be captured in the first nanopore 102 by the electric field (e.g., pointing upward) when the double strand molecule 107 is driven to the first side of the membrane 101 at block 415.

While the voltage of the voltage source 115 is applied and while the first single strand 105 of the double strand molecule 107 is being thread into the nanopore 102, the second single strand 106 of the double strand molecule 107 is captured in the second nanopore 103 by having the nanopore separation distance 104 between the first nanopore 102 and the second nanopore 103 corresponding to a strand separation distance (D) between the first single strand 105 and the second single strand 106, by having captured the first single strand 105 to limit diffusion of the second single strand 106, and/or by both at block 420.

The first single strand 105 in the first nanopore 102 and the second single strand 106 in the second nanopore 103 are individually stretched by (the force/pull of) the first single strand 105 and the second single strand 106 recombining (into the double strand molecule 108) on the second side of the membrane 101 in the bottom reservoir 165 at block 425.

The first strand in the first nanopore and the second strand in the second nanopore are single strands of the double strand molecule 107 that are stretched.

The first single strand 105 and the second single strand 106 recombining on the second side (bottom reservoir 165) of the membrane 101 includes the first single strand 105 and the second single strand 106 undergoing helical rewinding on the second side into a second double strand molecule 108 in the bottom reservoir 165. The energetics of hybridization drive the first single strand 105 and the second single strand 106 to undergo helical rewinding on the second side of the membrane 101. The hybridization of the first single strand 105 and the second single strand 106 on the second side generates a pull (e.g., downward force) on the first single strand 105 while in the first nanopore 102 and on the second single strand 106 while in the second nanopore 103. The pull by the hybridization on the second side is opposite a force (upward force) of unwinding of the first single strand 105 and the second single strand 106 of the double strand molecule 107 to cause the first single strand 105 and the second single strand to be stretched while in the first nanopore 102 and the second nanopore 103 respectively.

The nanopore separation distance 104 and the strand separation distance (D in FIG. 3) are substantially equal, and/or the nanopore separation distance 104 is smaller than the strand separation distance (D).

The first single strand 105 has an overhang (i.e., is longer) compared to the second single strand 106, and the overhang of the first strand enhances an initial capture of the first strand in the first nanopore 102.

A bow tie end (bow tie DNA 300) is ligated to the double strand molecule 107. The bow tie end comprises a first fork, a second fork, and a double strand stem ligated to the double strand molecule 107 (as shown in FIG. 3). The first single strand 105 is the first fork and the second single strand 106 is the second fork of the bow tie end ligated to the double strand molecule 107.

The first single strand 105 has a terminating end that is non-complementary to a terminating end of the second single strand 106.

The double strand molecule 107 is a deoxyribonucleic acid and/or is a ribonucleic acid. The bases of the first single strand 105 in the first nanopore 102 and bases of the second single strand 106 in the second nanopore 103 are sequenced, e.g., via respective tunneling currents measured by ammeters 205a and 205b. Bases of the first single strand 105 in the first nanopore 102 are sequenced concurrently while bases of the second single strand 106 in the second nanopore 103 are sequenced.

Note that a nanopore (also referred to a pore, nanochannel, hole, etc.) can be a small hole in the order of several nanometers (e.g., 4-8 nm) in internal diameter and/or the nanopore can be a larger hole in the order of a few microns (μm) in internal diameter. The theory behind nanopore sequencing is about what occurs when the nanopore is submerged in a conducting fluid (such as conductive solution 170) and an electric potential (voltage) is applied across the nanopore (e.g., via voltage source 115). The length of the nanopore corresponds to the thickness of the membrane 101 traversed by the nanopore 102. In one case, nanochannels are simply considered as nanopores of larger length. The size of the membrane 101 and the channels/nanopores 102 and 103 can be either small or quite large. When the membrane and corresponding channels/nanopores are large, the thickness of the membrane 101 and length of the nanopores 102, 103 may each be, e.g., 1-5 microns (μm). When the membrane and corresponding channels/nanopores are small, the thickness of the membrane 101 and length of the nanopores 102, 103 may each be, e.g., 4-8 nm.

Figure 5:
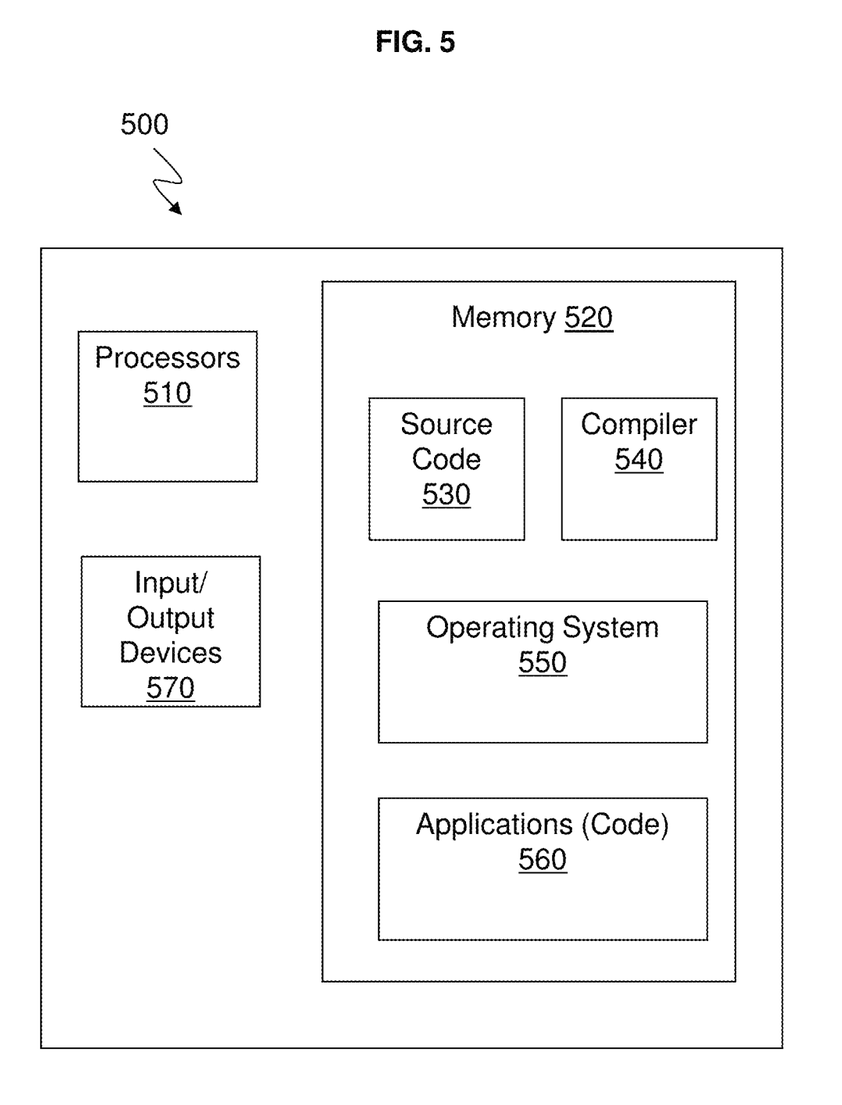
FIG. 5 is a block diagram that illustrates an example of a computer (computer test setup) having capabilities, which may be included in and/or combined with embodiments.

FIG. 5 illustrates an example of a computer 500 (e.g., as part of the computer test setup for testing and analysis) which may individually implement, control, and/or regulate the voltage of the voltage sources 115, 210a, 210b, and measurements of the ammeters 205a and 205b as discussed herein.

Various methods, procedures, modules, flow diagrams, tools, applications, circuits, elements, and techniques discussed herein may also incorporate and/or utilize the capabilities of the computer 500. Moreover, capabilities of the computer 500 may be utilized to implement features of exemplary embodiments discussed herein. One or more of the capabilities of the computer 500 may be utilized to implement, to connect to, and/or to support any element discussed herein (as understood by one skilled in the art) in FIGS. 1-4. For example, the computer 500 which may be any type of computing device and/or test equipment (including ammeters, voltage sources, connectors, etc.). Input/output device 570 (having proper software and hardware) of computer 500 may include and/or be coupled to the nanodevices and structures discussed herein via cables, plugs, wires, electrodes, patch clamps, etc. Also, the communication interface of the input/output devices 570 comprises hardware and software for communicating with, operatively connecting to, reading, and/or controlling voltage sources, ammeters, and current traces (e.g., magnitude and time duration of current), etc., as discussed herein. The user interfaces of the input/output device 570 may include, e.g., a track ball, mouse, pointing device, keyboard, touch screen, etc., for interacting with the computer 500, such as inputting information, making selections, independently controlling different voltages sources, and/or displaying, viewing and recording current traces for each base, molecule, biomolecules, etc.

Generally, in terms of hardware architecture, the computer 500 may include one or more processors 510, computer readable storage memory 520, and one or more input and/or output (I/O) devices 570 that are communicatively coupled via a local interface (not shown). The local interface can be, for example but not limited to, one or more buses or other wired or wireless connections, as is known in the art. The local interface may have additional elements, such as controllers, buffers (caches), drivers, repeaters, and receivers, to enable communications. Further, the local interface may include address, control, and/or data connections to enable appropriate communications among the aforementioned components.

The processor 510 is a hardware device for executing software that can be stored in the memory 520. The processor 510 can be virtually any custom made or commercially available processor, a central processing unit (CPU), a data signal processor (DSP), or an auxiliary processor among several processors associated with the computer 500, and the processor 510 may be a semiconductor based microprocessor (in the form of a microchip) or a macroprocessor.

The computer readable memory 520 can include any one or combination of volatile memory elements (e.g., random access memory (RAM), such as dynamic random access memory (DRAM), static random access memory (SRAM), etc.) and nonvolatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 520 may incorporate electronic, magnetic, optical, and/or other types of storage media. Note that the memory 520 can have a distributed architecture, where various components are situated remote from one another, but can be accessed by the processor 510.

The software in the computer readable memory 520 may include one or more separate programs, each of which comprises an ordered listing of executable instructions for implementing logical functions. The software in the memory 520 includes a suitable operating system (O/S) 550, compiler 540, source code 530, and one or more applications 560 of the exemplary embodiments. As illustrated, the application 560 comprises numerous functional components for implementing the features, processes, methods, functions, and operations of the exemplary embodiments.

The operating system 550 may control the execution of other computer programs, and provides scheduling, input-output control, file and data management, memory management, and communication control and related services.

The application 560 may be a source program, executable program (object code), script, or any other entity comprising a set of instructions to be performed. When a source program, then the program is usually translated via a compiler (such as the compiler 540), assembler, interpreter, or the like, which may or may not be included within the memory 520, so as to operate properly in connection with the O/S 550. Furthermore, the application 560 can be written as (a) an object oriented programming language, which has classes of data and methods, or (b) a procedure programming language, which has routines, subroutines, and/or functions.

The I/O devices 570 may include input devices (or peripherals) such as, for example but not limited to, a mouse, keyboard, scanner, microphone, camera, etc. Furthermore, the I/O devices 570 may also include output devices (or peripherals), for example but not limited to, a printer, display, etc. Finally, the I/O devices 570 may further include devices that communicate both inputs and outputs, for instance but not limited to, a NIC or modulator/demodulator (for accessing remote devices, other files, devices, systems, or a network), a radio frequency (RF) or other transceiver, a telephonic interface, a bridge, a router, etc. The I/O devices 570 also include components for communicating over various networks, such as the Internet or an intranet. The I/O devices 570 may be connected to and/or communicate with the processor 510 utilizing Bluetooth connections and cables (via, e.g., Universal Serial Bus (USB) ports, serial ports, parallel ports, FireWire, HDMI (High-Definition Multimedia Interface), etc.).

In exemplary embodiments, where the application 560 is implemented in hardware, the application 560 can be implemented with any one or a combination of the following technologies, which are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

As used herein, polynucleotides include DNA and RNA, and are polymeric, contiguous, i.e., covalently bonded, strands of nucleotides.

"Complementary" or "substantially complementary" refers to the hybridization or base pairing or the formation of a duplex between nucleotides or nucleic acids, such as, for instance, between the two strands of a double-stranded DNA molecule or between an oligonucleotide primer and a primer binding site on a single stranded nucleic acid. Complementary nucleotides are, generally, A and T (or A and U), or C and G. Two single stranded RNA or DNA molecules are said to be substantially complementary when the nucleotides of one strand, optimally aligned and compared and with appropriate nucleotide insertions or deletions, pair with at least about 80% of the nucleotides of the other strand, usually at least about 90% to 95%, and more specifically about 98 to 100%. Alternatively, substantial complementarity exists when an RNA or DNA strand will hybridize under selective hybridization conditions to its complement. Typically, selective hybridization will occur when there is at least 65% complementary over a stretch of at least 14 to 25 nucleotides, specifically at least about 75%, more specifically at least about 90% complementary.

The term "single stranded DNA" (ssDNA) as used herein refers to a naturally occurring or synthetic deoxyribonucleic acid molecule comprising a linear single strand, for example, a ssDNA can be a sense or antisense gene sequence.

"Duplex" is used interchangeably with "double-stranded" and means at least two oligonucleotides and/or polynucleotides that are fully or partially complementary and that undergo Watson-Crick type base pairing among all or most of their nucleotides so that a stable complex is formed. The terms "annealing" and "hybridization" are used interchangeably to mean the formation of a stable duplex. In one aspect, stable duplex means that a duplex structure is not destroyed by a stringent wash, e.g., conditions including temperature of about 5° C. less that the $T_m$ (melting temperature) of a strand of the duplex and low monovalent salt concentration, e.g., less than 0.2 M, or less than 0.1 M. "Perfectly matched" in reference to a duplex means that the poly- or oligonucleotide strands making up the duplex from a double Watson-Crick basepairing with a nucleotide in the other strand. The term "duplex" includes the pairing of nucleoside analogs, such as deoxyinosine, nucleosides with 2-aminopurine bases, PNAs, and the like, that may be employed. A "mismatch" in a duplex between two oligonucleotides or polynucleotides means that at pair of nucleotides in the duplex fails to undergo Watson-Crick bonding.

"Hybridization" refers to the process in which two single-stranded polynucleotides bind non-covalently to form a stable double-stranded or duplex polynucleotide. The term "hybridization" may also refer to triple-stranded hybridization. The resulting (usually) double-stranded polynucleotide is a "hybrid" or "duplex." "Hybridization conditions" will typically include salt concentrations of less than about 1 M, more usually less than about 500 mM or less than about 200 mM. Hybridization temperatures can be as low as 5° C., but are typically greater than 22° C., more typically greater than about 30° C., and specifically in excess of about 37° C.

Hybridizations are usually performed under stringent conditions, i.e., conditions under which a probe will specifically hybridize to its target subsequence. Stringent conditions are sequence-dependent and are different in different circumstances. Longer fragments may require higher hybridization temperatures for specific hybridization. As other factors may affect the stringency of hybridization, including base composition and length of the complementary strands, presence of organic solvents and extent of base mismatching, the combination of parameters is more important than the absolute measure of any one alone. Generally, stringent conditions are selected to be about 5° C. lower than the $T_m$ for the specific sequence at a defined ionic strength and pH. Exemplary stringent conditions include salt concentration of at least 0.01 M to no more than 1 M Na ion concentration (or other salts) at a pH 7.0 to 8.3 and a temperature of at least 25° C. For example, conditions of 5×SSPE (750 mM NaCl, 5.0 mM sodium phosphate, 5 mM EDTA, pH 7.4) and a temperature of 25-30° C. are suitable for allele-specific probe hybridizations. "Hybridizing specifically to" or "specifically hybridizing to" or like expressions refer to the binding, duplexing, or hybridizing of a molecule substantially to or only to a particular nucleotide sequence or sequences under stringent conditions when that sequence is present in a complex mixture (e.g., total cellular) DNA or RNA.

The term "blunt end" as used herein refers to the end of a dsDNA molecule having 5' and 3' ends, wherein the 5' and 3' ends terminate at the same nucleotide position. Thus, the blunt end comprises no 5' or 3' overhang.

"Ligation" means to form a covalent bond or linkage between the termini of two or more nucleic acids, e.g. oligonucleotide and/or polynucleotide. Ligation included blunt-end ligation as well as ligation with a single strand overhang. The nature of the bond or linkage may vary widely and the ligation may be carried out enzymatically or chemically. In one embodiment, ligations are carried out enzymatically to form a phosphodiester linkage between a 5' carbon of a terminal nucleotide of one oligonucleotide with 3' carbon of another oligonucleotide. Examples of ligases include Taq DNA ligase, T4 DNA ligase, T7 DNA ligase, and *E. coli* DNA ligase. The choice of the ligase depends to a certain degree on the design of the ends to be joined together. Thus, if the ends are blunt, T4 DNA ligase may be employed, while a Taq DNA ligase may be preferred for a sticky end ligation, i.e. a ligation in which an overhang on each end is a complement to each other.

As used herein, a "target polynucleotide" or "target DNA" is a polynucleotide from a sample. In one embodiment, a target polynucleotide is a double stranded polynucleotide (e.g., DNA) for which the nucleotide sequence is to be determined.

A sample may be collected from an organism, mineral or geological site (e.g., soil, rock, mineral deposit, combat theater), forensic site (e.g., crime scene, contraband or suspected contraband), or a paleontological or archeological site (e.g., fossil, or bone) for example. A sample may be a "biological sample," which refers to a material obtained from a living source or formerly-living source, for example, an animal such as a human or other mammal, a plant, a bacterium, a fungus, a protist or a virus. The biological sample can be in any form, including without limitation a solid material such as a tissue, cells, a cell pellet, a cell extract, or a biopsy, or a biological fluid such as urine, blood including plasma or serum, saliva, amniotic fluid, exudate from a region of infection or inflammation, or a mouth wash containing buccal cells, urine, cerebral spinal fluid and synovial fluid and organs.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated The flow diagrams depicted herein are just one example. There may be many variations to this diagram or the steps (or operations) described therein without departing from the spirit of the invention. For instance, the steps may be performed in a differing order or steps may be added, deleted or modified. All of these variations are considered a part of the claimed invention.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

What is claimed is:

1. A method for presenting single strands of a double strand molecule to a membrane, the method comprising:
    driving the double strand molecule to a first side of the membrane by an electric field, the membrane comprising a first nanopore and a second nanopore spaced apart by a nanopore separation distance, the membrane comprising a second side opposite the first side;
    wherein the double strand molecule comprises a first strand and a second strand when driven to the first side of the membrane;
    causing the first strand of the double strand molecule to be captured in the first nanopore by the electric field when the double strand molecule is driven to the first side of the membrane;
    causing the second strand of the double strand molecule to be captured in the second nanopore by having the nanopore separation distance between the first nanopore and the second nanopore corresponding to a strand separation distance between the first strand and the second strand, by having captured the first strand to limit diffusion of the second strand, or both by having the nanopore separation distance between the first nanopore and the second nanopore corresponding to a strand separation distance between the first strand and the second strand and by having captured the first strand to limit diffusion of the second strand; and
    individually stretching the first strand in the first nanopore and the second strand in the second nanopore which is caused by the first strand and the second strand recombining on the second side of the membrane.

2. The method of claim 1, wherein the first strand in the first nanopore and the second strand in the second nanopore are single strands and stretched.

3. The method of claim 1, wherein the first strand and second strand recombining on the second side of the membrane comprises the first strand and the second strand undergoing helical rewinding on the second side into a second double strand molecule.

4. The method of claim 3, wherein energetics of hybridization drive the first strand and the second strand to undergo the helical rewinding on the second side of the membrane.

5. The method of claim 4, wherein the hybridization of the first strand and the second strand on the second side generates a pull on the first strand while in the first nanopore and on the second strand while in the second nanopore;
    wherein the pull by the hybridization on the second side is opposite a force of unwinding of the first strand and the second strand of the double strand molecule to cause the first strand and the second strand to be stretched while in the first nanopore and the second nanopore respectively.

6. The method of claim 1, wherein the nanopore separation distance and the strand separation distance are substantially equal; or
    wherein the nanopore separation distance is smaller than the strand separation distance.

7. The method of claim 1, wherein the first strand has an overhang compared to the second strand, the overhang of the first strand enhances an initial capture of the first strand in the first nanopore.

8. The method of claim 1, wherein a bow tie end is ligated to the double strand molecule;
    wherein the bow tie end comprises a first fork, a second fork, and a double strand stem, the double strand stem being ligated to the double strand molecule; and
    wherein the first strand is the first fork and the second strand is the second fork of the bow tie end ligated to the double strand molecule.

9. The method of claim 1, wherein the first strand has a terminating end that is non-complementary to a terminating end of the second strand.

10. The method of claim 1, wherein the double strand molecule is a deoxyribonucleic.

11. The method of claim 1, wherein the double strand molecule is a ribonucleic acid.

12. The method of claim 1, further comprising sequencing the first strand in the first nanopore and the second strand in the second nanopore;
    wherein when a thickness of the membrane ranges from 4 to 8 nanometers, each length of the first nanopore and the second nanopore correspondingly ranges from 4 to 8 nanometers.

13. The method of claim 1, further comprising sequencing bases of the first strand in the first nanopore while sequencing bases of the second strand in the second nanopore.

14. The method of claim 1, wherein when the thickness of the membrane ranges from 1 to 5 microns, each length of the first nanopore and the second nanopore correspondingly ranges from 1 to 5 microns.

* * * * *